United States Patent [19]

Petrzilka

[11] 4,247,717
[45] Jan. 27, 1981

[54] ORGANO-SELENENYL COMPOUND AND METHOD FOR ITS PREPARATION

[75] Inventor: Martin Petrzilka, Puplinge, Geneva, Switzerland

[73] Assignee: Firmenich SA, Geneva, Switzerland

[21] Appl. No.: 73,329

[22] Filed: Sep. 7, 1979

[30] Foreign Application Priority Data

Sep. 21, 1978 [CH] Switzerland .................... 9858/78

[51] Int. Cl.$^3$ .............................................. C07C 47/228
[52] U.S. Cl. .................................................. 568/425
[58] Field of Search ........................... 260/601 R, 599; 568/425

[56] References Cited

PUBLICATIONS

Sharpless et al., "J. Amer. Chem. Soc.", vol. 95, (1973), pp. 2697, 6137-6139.
Sharpless et al., "Tetrahedron Letters", (1973), pp. 1979-1982, Pergman Press.
Leonard-Coppens et al., "Tetrahedron Letters", #36, pp. 3227-3230, (1976), Pergamon Press, Great Britain.
Remion et al., "Tetrahedron Letters", #17, pp. 1385-1388, (1976), Pergamon Press, Great Britain.

*Primary Examiner*—Werren B. Lone
*Attorney, Agent, or Firm*—Scully, Scott, Murphy & Presser

[57] ABSTRACT

New organo-selenenyl aldehyde of formula $C_6H_5$-Se-$CH_2$-CHO and method for its preparation.

The new compound is a useful starting material for the preparation of allylic alcohols, epoxydes or olefines.

1 Claim, No Drawings

ORGANO-SELENENYL COMPOUND AND METHOD FOR ITS PREPARATION

BACKGROUND OF THE INVENTION

Recent investigations have shown the particular utility presented by certain organo-selenenyl derivatives as selected intermediates in various syntheses. More precisely, it could be established that certain β-hydroxy-selenenyl compounds of formula

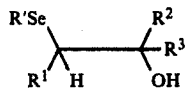

wherein R' defines a lower alkyl radical or an aryl group and $R^1$, $R^2$ and $R^3$ each represents an alkyl radical or a hydrogen atom, constitute very useful starting materials for the preparation of allyl alcohols, epoxydes or olefines [see e.g.: J. Amer. Chem. Soc., 95, 2697 (1973); Angew. Chem. Int. Ed. 13, 804 (1974); idem 13, 805 (1974); Tetrahedron Letters, 1385 and 3743 (1976); J. Chem. Soc. Chem. Comm. 790 (1975); Angew. Chem. Int. Ed. 14, 700 (1975)].

Said β-hydroxy compounds could be synthesized by a regiospecific and stereoselective synthesis starting from an α-seleno-aldehyde or -ketone by reduction with lithium aluminiumhydride or by means of a Grignard type reagent [see: Tetrahedron Letters, 3227 (1976)].

α-Seleno-aldehydes and α-seleno-ketones have been prepared in the past via the process described by K. B. Sharpless et al., namely as described in J. Amer. Chem. Soc., 95, 6137 (1973). According to these authors, α-phenyl-seleno-carbonyl derivatives of formula

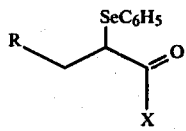

wherein symbol R represents an alkyl or an aryl radical and X defines a hydrogen atom or an alkyl group, can be obtained by treating a ketone or an aldehyde with the reagents such as phenyl-selenenyl chloride or bromide.

By applying this process to the synthesis of the desired selenenyl derivative of acetaldehyde, one is faced with major difficulties. The reaction in fact ought to be carried out in a strongly acidic medium and it is known that under these reaction conditions, acetaldehyde undergoes aldolisation, hence a marked reduction in the yield of the end products.

THE INVENTION

We have now discovered that it was possible to prepare the compound of formula

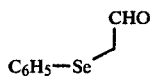

by a process which comprises subsequently a. adding, in the presence of an aliphatic alcohol, a phenylselenenyl halide to a vinyl ether of formula

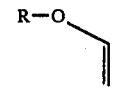

wherein symbol R represents an alkyl radical, and b. treating the thus formed acetal with an acidic agent.

As phenyl-selenenyl halide, phenyl-selenenyl chloride or bromide are preferred. The addition as per step a. above is effected at room temperature and preferably in a polar organic solvent, such as a hydroxylic solvent or a chlorinated hydrocarbon. To this end ethanol is perfectly adapted as it acts as both solvent and reagent.

As vinyl ether of formula (II) one can use for instance methyl- or ethyl-vinyl ether.

The subsequent step of the process of the invention, which formally consists in treating the obtained acetal with an acidic agent, is carried out by means of a mineral protic acid, such as hydrochloric acid, or an organic acid, e.g. p-toluenesulfonic acid, or an acidic diatomaceous earth. Thus, according to a preferred embodiment of the invention process, phenyl-seleno-acetaldehyde diethyl-acetal in ether solution was treated with a 1 N aqueous HCl solution to give, after the usual work-up of the organic phase, the desired phenyl-seleno-acetaldehyde.

As indicated above, phenyl-seleno-acetaldehyde is a novel compound. It represents a particularly useful starting material, namely for the preparation of β-hydroxy-phenylselenenyl derivatives of formula

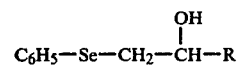

R = alkyl, H

Said derivatives could be prepared by treating phenyl-seleno-acetaldehyde with an alkyl magnesium halide.

The invention is better illustrated by but not limited to the following example wherein the temperatures are indicated in degrees centigrade.

EXAMPLE

Phenyl-seleno-acetaldehyde a. 2.1 ml (22 mmole) of ethyl-vinyl ether were added, under stirring at 25° and under an argon atmosphere, to a solution of 4.72 g (20 mmole) of benzene-selenenyl bromide in 50 ml of ethanol. The color of the reaction mixture changed during the addition and, from dark orange, went to light yellow. After having been left for ten supplementary minutes under stirring, the resulting mixture was poured into a saturated aqueous solution of sodium bicarbonate and extracted with 3 fractions of ether. The combined organic extracts were washed with a sodium bicarbonate aqueous solution and with brine, then they were dried over $K_2CO_3$ and concentrated under vacuum to give 5.25 g (yield 96%) of the desired product under the form of a slightly yellow colored oil having b.p. 80°-2°/0.1 Torr.

b. A two phase mixture, constituted by a solution of 22.6 g (83 mmole) of the compound obtained as indicated under letter b. above in 500 ml of diethyl ether and 500 ml of a 1 N aqueous HCl solution, was kept under stirring for 24 hours. After separation, the organic layer was combined with the ethereal extracts obtained by the extraction of the aqueous phase with ether, and subjected to the usual workup (washing, neutralisation and drying). The evaporation of the volatile fraction gave 16.1 g (yield 98%) of the desired product; b.p. 56°–7°/0.01 Torr.

The analytical data of it were the following:

IR (CCl$_4$): 2715, 1710, 1580, 1480, 1148, 1025, 948, 692 and 675 cm$^{-1}$;

NMR (CDCl$_3$/100 MHz): 3.54 (d, J=4 Hz, 2H); 7.20–7.66 (m, 5H); 9.54 (t, J=4 Hz, 1H) δppm;

MS: M$^+$=220 and 198; m/e: 171, 169, 157, 91, 77, 65, 51.

What I claim is:

1. Phenyl-seleno-acetaldehyde of formula $$C_6H_5-SeCH_2-CHO \qquad (1).$$

* * * * *